US00PP16497P2

(12) United States Plant Patent
Olesen

(10) Patent No.: US PP16,497 P2
(45) Date of Patent: May 2, 2006

(54) MINIATURE ROSE PLANT NAMED 'POULPAH028'

(50) Latin Name: ***Rosa* hybrid**
Varietal Denomination: Poulpah028

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 11/002,361

(22) Filed: Dec. 1, 2004

(51) Int. Cl.
*A01H 5/00* (2006.01)

(52) U.S. Cl. ..... Plt./119

(58) Field of Classification Search ..... Plt./119, Plt./120, 122

See application file for complete search history.

*Primary Examiner*—Anne Marie Grunberg
*Assistant Examiner*—June Hwu

(57) ABSTRACT

A new rose plant that has abundant, orange red flowers and attractive glossy foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpah028'.

SUMMARY OF THE INVENTION

The present invention constitutes a new and distinct variety of miniature rose plant which originated from a controlled crossing between the female seed parent, an unnamed seedling, and the male pollen parent named 'Poulac006', a rose by the same inventor described and illustrated in U.S. Plant patent application Ser. No. 10/342,702 dated Jan. 14, 2003 (now abandoned). The two parents were crossed and the resulting seeds were planted in a controlled environment. The new variety is named 'Poulpah028'.

The new rose may be distinguished from the female seed parent by the following combination of characteristics:

1. 'Poulpah028' has 45 to 50 petals; whereas, the female parent has 35 petals.
2. 'Poulpah028' has orange red flowers. The female parent has pink flowers.

The new variety may be distinguished from its pollen parent, 'Poulac006', by the following combination of characteristics:

1. 'Poulpah028' has 45 to 50 petals, while 'Poulac006' has 35 to 40 petals.
2. 'Poulpah028' has a bloom diameter of 60 to 70 mm while 'Poulac006' has a bloom diameter of 60 to 80 mm.
3. Petal spots of 'Poulpah028' are Yellow Group 2B to 2C. Petal spots of 'Poulac006' are Yellow Group 12B.

The objective of the hybridization of this rose variety for commercial culture was to create a new and distinct variety with unique qualities, such as:

1. Uniform and abundant orange red flowers;
2. Vigorous and compact growth;
3. Year-round flowering under glasshouse conditions;
4. Suitability for production from softwood cuttings in pots;

5. Durable flowers and foliage which make a variety suitable for distribution in the floral industry.

This combination of qualities is not present in previously available commercial cultivars of this type, known to the inventor, and distinguish 'Poulpah028' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpah028' was selected by the inventor as a single plant from the progeny of the hybridization in June 2001.

Asexual reproduction of 'Poulpah028' by cuttings and traditional budding was first done by Mogens N. Olesen in the nursery in Fredensborg, Denmark in April 2002. This initial and other subsequent propagations conducted in controlled environments have demonstrated that the characteristics of 'Poulpah028' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah028'. Specifically illustrated in the drawing:

FIG. 1.1; Flower buds at various stages of development;

FIG. 1.2; Open flower, above view;

FIG. 1.3; Sepals, receptacle, and pedicel;

FIG. 1.4; Open flower showing attachment of leaves buds and pedicels;

FIG. 1.5; Juvenile leaves;

FIG. 1.6; Mature leaves;

FIG. 1.7; Petals detached;

FIG. 1.8; Bare stem.

DETAILED DESCRIPTION OF THE VARIETY

The following is a description of 'Poulpah028', as observed in its growth in glasshouses in Odense, Denmark. Observed plants are 4 months of age, and were cultivated in 15 cm pots. Color references are made using The Royal Horticultural Society (London, England) Colour Chart, 2001, except where common terms of color are used.

For a comparison, several physical characteristics of the rose variety 'Poulac011', described and illustrated in U.S. Plant Pat. No. 15,821 issued on Jun. 28, 2005, are detailed in Chart 1.

CHART 1

| | 'Poulpah028' | 'Poulac011' |
|---|---|---|
| Petalage | 45 to 50 petals. | 40 petals. |
| Bud color as sepals unfold. | Orange-Red Group 34A. | Red Group 53D |
| General Tonality | Red Group 40A. | Red Group 52A to 52B with light intonations of Red-Purple Group 67B |

FLOWER AND FLOWER BUD

Blooming habit: Continuous.

Flower bud:

*Size.*—Upon opening, 20 mm in length from base of receptacle to end of bud. 11 mm in diameter.

*Bud form.*—Urceolate.

*Bud color.*—As sepals unfold, petals are Orange-Red Group 34A.

*Sepals.*—Upper Surface: Color: Green Group 138A changing to Green Group 138C at the sepal base. Surface: Somewhat pubescent. Lower Surface: Color: Yellow-Green Group 144A. Anthocyanic pigments Greyed-Red 180A at apecies of foliaceous appendages. Texture: Smooth. Shape: Apex: Normally cirrhose. Occasionally, sepals broaden at the apex to a width of 5 mm. Base: Flat at union with receptacle. Margins: Margins have strong to medium foliaceous appendages. Stipitate glands present at margins. Size: 25 to 40 mm (l) by 7 mm (w).

*Receptacle.*—Surface Texture: Smooth. Shape: Urn-shaped. Size: 6 mm (h)×8 mm (w). Color: Green Group 143A.

*Pedicel.*—Surface: Smooth. Length: 20 to 30 mm average. Diameter: 3 mm. Color: Green Group 143A. Strength: Strong.

*Borne.*—Singularly and in clusters of 3 flower buds per stem. Inflorescence type is a corymb.

Flower bloom:

*Fragrance.*—Light floral scent.

*Duration.*—As a pot plant, flowers last 15 to 20 days. Petals do not fall cleanly away from plant after flowers mature.

*Size.*—Average flower diameter is 60 to 70 mm when open. Depth is 30 to 35 mm.

*Form.*—As sepals unfold petals remain tightly closed. Afterwards, flowers open completely resembling a pom pom.

*Shape of flower when viewed from the side.*—Upon opening, upper part: Pointed. Upon opening, lower part: Flat. Open flower, upper part: Convex. Open flower, lower part: Concave.

Petalage: Average range is 45 to 50 petals total. 5 to 8 of which are petaloids.

Petal color:

*Upon opening, petals.*—Outermost petals: Upper Surface: Red Group 40A to Red Group 44B. Lower Surface: Red Group 43B. Innermost petals: Upper Surface: Red Group 40A to Red Group 44B. Lower Surface: Red Group 43B.

*Upon opening, basal petal spots.*—Upper Surface: Yellow Group 2B. Lower Surface: Yellow Group 2C.

*After opening, petals.*—Outermost petals: Upper Surface: Red Group 40A. Lower Surface: Red Group 43B with intonations of Red Group 43C with occasional streaks of Red Group 55C to Green-White Group 157A. Innermost petals: Upper Surface: Red Group 40A. Lower Surface: Red Group 43B with intonations of Red Group 43C with occasional streaks of Red Group 55C to Green-White Group 157A.

*After opening, basal petal spots.*—Outermost petals: Upper Surface: Green-White Group 157A to Yellow Group 2C. Lower Surface: Green-White Group 157A to Yellow Group 2C.

General tonality: On open flower Red Group 40A. No change in the general tonality at the end of the $15^{th}$ day.

Petals:

*Petal reflex.*—Reflexed.

*Petal margin.*—Entire and uniform undulations of margin observed.

*Shape.*—Broad elliptical. Base: Acute. Apex: Rounded.

*Size.*—On average, 37 (l)×32 mm (w).

*Texture.*—Smooth.

*Thickness.*—Average.

*Arrangement.*—Not formal.

Petaloids:

*Size.*—30 mm (l)×20 mm (w).

*Shape.*—Rounded to elliptical. Base is slender and pointed. Apex is rounded. Margins are undulated.

*Color.*—Upper and undersurfaces are Red Group 40A.

Reproductive organs:

*Pollen.*—None observed.

*Anthers.*—Size: 3 mm long. Color: Yellow-Orange Group 22A. Quantity: 120 to 130.

*Filaments.*—Color: At the base, Yellow Group 3A. Toward the anther, Greyed-Red Group 180A. Length: 6 mm.

*Pistils.*—Length: 8 mm. Quantity: 90 to 100.

*Stigmas.*—Superior relative to the length of the filaments and the height of the anthers. Color: Greyed-Yellow Group 160C.

*Styles.*—Color: Greyed-Yellow Group 160C with intonations of Red-Purple Group 58C.

*Seed.*—None observed.

PLANT

Plant growth: Upright to bushy. When grown as a 15 cm pot plant on its own roots, the average height of the plant itself is 20 to 25 cm and the average width is 15 to 20 cm.

Stems:

*Color.*—Young wood: Yellow-Green Group 145A. Older wood: Yellow-Green Group 144A to 144B.

*Diameter.*—3 mm.

*Internodal distance.*—20 mm.

*Length of stems.*—On average canes are 20 cm from the base of the stem to the flowering portion.

*Surface texture.*—Young wood: Smooth. Older wood: Smooth.

Thorns:

*Incidence.*—10 to 14 per 10 cm of stem.

*Color.*—Greyed-Red Group 180D.

*Shape.*—Upper side: Flat. Lower side: Concave.

Plant foliage: Normal number of leaflets on normal leaves in middle of the stem is 5 leaflets.

*Compound leaf size.*—85 to 95 mm (l)×60 to 65 mm (w).

*Quantity.*—5 leaves per 10 cm of stem.

*Color.*—Juvenile foliage: Upper surface is Yellow-Green Group 144A with anthocyanic intonations the color of Greyed-Orange Group 176A. Undersurfaces are Yellow-Green Group 144A with anthocyanic intonations the color of Greyed-Orange Group 176A. Mature foliage: Upper surface is Yellow-Green Group 147A. Undersurfaces are Yellow-Green Group 147B with faint anthocyanic intonations Greyed-Orange 176A.

Plant leaves and leaflets:

*Stipules.*—Size: 8 mm in length. Shape: Linear, slightly broad based with outward extending apecies. Margins: Finely serrated with few stipitate glands. Color: Yellow-Green Group 144B.

*Petiole.*—Length: 20 mm. Diameter: 1.5 mm. Color: Upper surface: Greyed-Orange Group 176A. Lower surface: Yellow-Green Group 145B. Underneath: Few small prickles observed at margins.

*Rachis.*—Length: 27 mm. Color: Yellow-Green Group 144B with strong intonations of Greyed-Orange Group 176A. Underneath: Few small prickles and stipitate glands observed.

*Leaflet.*—Size: 45 to 50 mm (l)×28 to 30 mm (w). Edge: Serrated. General Shape: Ovate. Apex Shape: Acuminate. Base Shape: Rounded. Texture: Smooth. Thickness: Average. Arrangement: Odd pinnate. Venation: Reticulate. Leaf Gloss: Very glossy.

Disease resistance: Average resistance to powdery mildew, black spot, and *Botrytis* under normal growing conditions in Fredensborg, Denmark.

It is claimed:

1. A new and distinct variety of rose plant of the miniature class named 'Poulpah028', substantially as illustrated and described herein, due to its abundant, orange red flowers, glossy foliage, vigorous growth, compact habit, suitability for production from softwood cuttings in pots, and durable flowers and foliage that make the variety suitable for distribution in the floral industry.

* * * * *

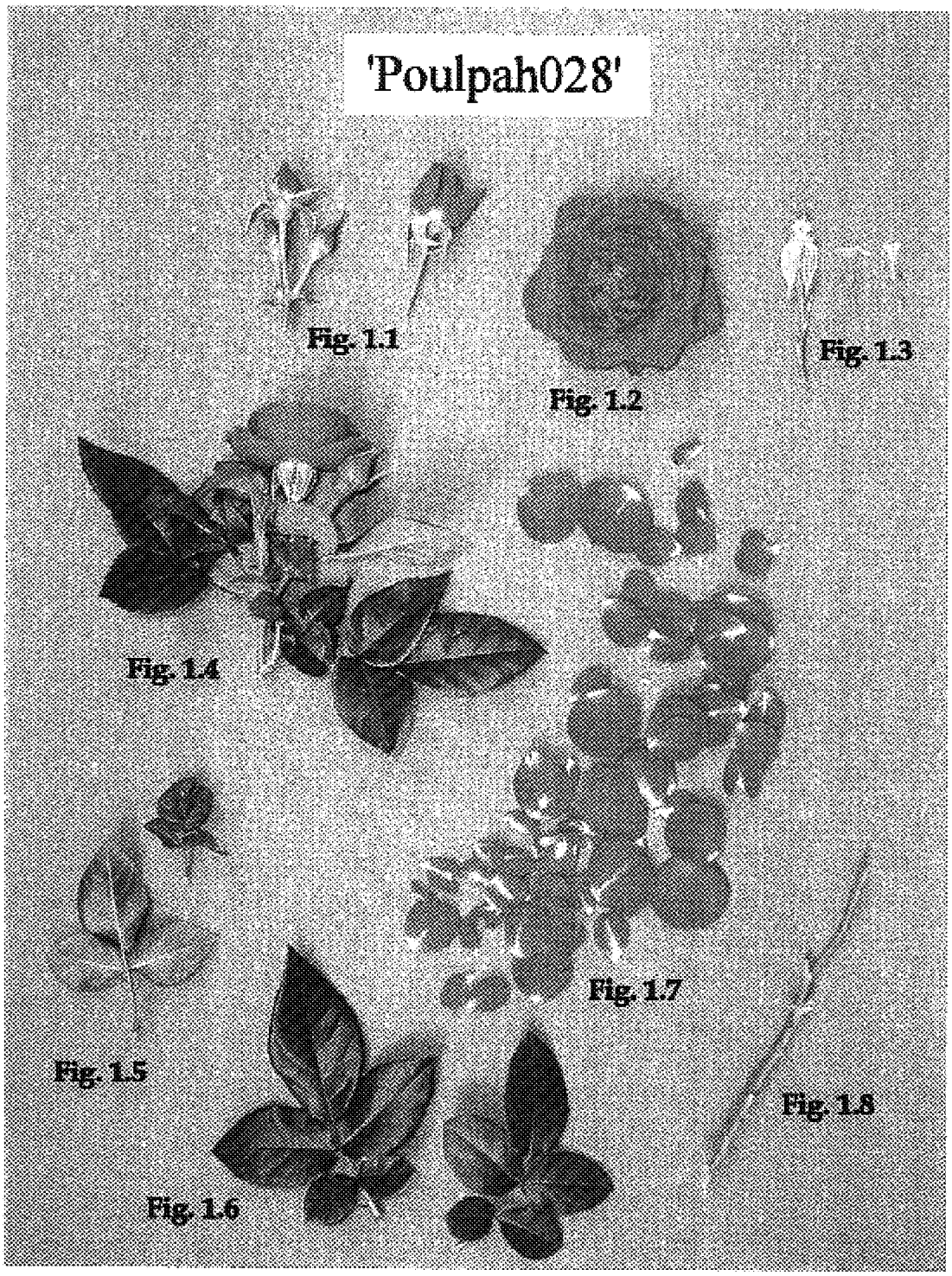
'Poulpah028'
Fig. 1.1
Fig. 1.2
Fig. 1.3
Fig. 1.4
Fig. 1.5
Fig. 1.6
Fig. 1.7
Fig. 1.8